United States Patent
Govil et al.

(10) Patent No.: US 12,194,194 B2
(45) Date of Patent: *Jan. 14, 2025

(54) SOFT TISSUE PROTEIN COMPOSITIONS, METHODS OF MAKING, AND USES THEREOF

(71) Applicant: Advanced Biologics, LLC, Carlsbad, CA (US)

(72) Inventors: Amit Prakash Govil, Carlsbad, CA (US); Bryan Choi, Carlsbad, CA (US); Sahil Jalota, Carlsbad, CA (US)

(73) Assignee: Advanced Biologics, LLC, Carlsbad, CA (US)

( * ) Notice: Subject to any disclaimer, the term of this patent is extended or adjusted under 35 U.S.C. 154(b) by 5 days.

This patent is subject to a terminal disclaimer.

(21) Appl. No.: 17/577,519

(22) Filed: Jan. 18, 2022

(65) Prior Publication Data

US 2022/0152277 A1    May 19, 2022

Related U.S. Application Data

(62) Division of application No. 15/767,957, filed as application No. PCT/US2016/056675 on Oct. 12, 2016, now Pat. No. 11,253,631.

(60) Provisional application No. 62/240,345, filed on Oct. 12, 2015.

(51) Int. Cl.
| | | |
|---|---|---|
| *A61L 27/36* | (2006.01) | |
| *A23J 1/02* | (2006.01) | |
| *A23J 1/04* | (2006.01) | |
| *A61L 27/44* | (2006.01) | |

(52) U.S. Cl.
CPC ............. *A61L 27/3687* (2013.01); *A23J 1/02* (2013.01); *A23J 1/04* (2013.01); *A61L 27/3604* (2013.01); *A61L 27/44* (2013.01); *A61L 2430/34* (2013.01); *A61L 2430/40* (2013.01)

(58) Field of Classification Search
None
See application file for complete search history.

(56) References Cited

U.S. PATENT DOCUMENTS

| | | |
|---|---|---|
| 2011/0151011 A1 | 6/2011 | Flynn |
| 2012/0264190 A1 | 10/2012 | Christman et al. |
| 2013/0202563 A1 | 8/2013 | Badylak et al. |
| 2013/0273658 A1 | 10/2013 | Damm et al. |

OTHER PUBLICATIONS

Depalma, "Focus on Cell Disruption," Lab Manager, Product Focus (Jun. 2015).
Chen, et al., "Advancing biomatierals of human origin for tissue engineering," Progress in Polymer Science, vol. 53 (2015) pp. 86-168.
Kleinig, "Cell Disruption Mechanisms," University of Adelaide, 1997, pp. 1-223.
International Search Report for PCT/US2016/056575 of Jan. 12, 2017.
Choi, et al, "Decellularized Extracellular Matrix Derived from Porcine Adipose Tissue as a Xenogeneic Biomaterial for Tissue Engineering," Tissue Engineering C 18(11), 2012, pp. 866-876.
Choi, et al., "Human extracellular matrix (ECM) powders for injectable cell delivery and adipose tissue engineering," J. Controlled Release 129 (2009) pp. 2-7.
Choi, et al., "Adipose Tissue: A valuable Resource of Biomaterials for Soft Tissue Engineering," Macromolecular Research 22(9), (2014) pp. 932-947.

*Primary Examiner* — Teresa E Knight
(74) *Attorney, Agent, or Firm* — Thomas | Horstemeyer, LLP

(57) ABSTRACT

Provided herein are soluble soft tissue protein compositions that can contain one or more soft-tissue bioactive factors, methods of making the soluble soft tissue protein compositions, and methods of using the soluble soft tissue protein compositions.

16 Claims, 11 Drawing Sheets

SOFT TISSUE PROTEIN COMPOSITIONS, METHODS OF MAKING, AND USES THEREOF

CROSS-REFERENCE TO RELATED APPLICATIONS

This application is a divisional of U.S. application Ser. No. 15/757,957, filed Apr. 12, 2018, which is a 35 U.S.C. § 371 national stage application of PCT Application No. PCT/US2016/056575, filed Oct. 12, 2016, which claims benefit of U.S. Provisional Application No. 62/240,345, filed Oct. 12, 2015, all of which are herein incorporated by reference in their entireties.

BACKGROUND

Soft tissue grafting and implants play a role in cosmetic, reconstructive, and dental procedures. As such, there exists a need for compositions that can be used in soft tissue grafting and implants.

SUMMARY

Provided herein are methods of making a soluble soft tissue protein composition that can include the steps of harvesting soft tissue from a donor to obtain harvested soft tissue, where the soft tissue contains soft tissue cells; heating the harvested soft tissue to at least 20° C.; and lysing the soft tissue cells to obtain a soft tissue cell lysate to yield the soluble soft tissue protein composition. The method can further include the step of fractionating the soft tissue cell lysate via centrifugation to obtain a soluble soft tissue protein fraction after lysing the soft tissue cells. The method can further include the step of dehydrating the soluble soft tissue lysate to obtain a dehydrated soluble soft tissue protein composition. The step of heating the harvested soft tissue can occur at about 20° C. to about 40° C. The method can further include the step of washing the harvested soft tissue. In some embodiments, the steps of washing the harvested soft tissue, heating the harvested soft tissue, and lysing soft tissue cells can occur simultaneously. The method can further include the step of adding a stabilization solution prior to dehydrating. The method can further include the step of filtering the soluble soft tissue protein fraction. The method can further include the step selectively filtering or isolating the soft tissue cells to obtain a desired cell population prior to lysing the soft tissue cells. The step of lysing can include lysing the desired cell population. The desired cell population can be adipocytes. The dehydrated soluble soft tissue protein composition can be implanted in or otherwise administered to a subject in need thereof. In embodiments, an amount of the dehydrated soluble soft tissue protein composition in stabilization solution can be implanted in or otherwise administered to a subject in need thereof. The method can further include the step of applying an amount of the dehydrated soluble soft tissue protein composition to a scaffold. The scaffold can be implanted in or otherwise administered to a subject in need thereof. The method can further include the step of applying an amount of the dehydrated soluble soft tissue protein composition in stabilization solution to a scaffold. The scaffold can be implanted in or otherwise administered to a subject in need thereof.

Also provided herein are soluble soft tissue protein compositions that can contain a bioactive factor, where the soluble soft tissue protein composition is made by a method that can include the steps of methods of making a soluble soft tissue protein composition that can include the steps of harvesting soft tissue from a donor to obtain harvested soft tissue, where the soft tissue contains soft tissue cells; heating the harvested soft tissue to at least 20° C.; and lysing the soft tissue cells to obtain a soft tissue cell lysate to yield the soluble soft tissue protein composition.

Also provided herein are methods of treating a subject in need thereof that can contain the step of implanting or administering a soluble soft tissue protein composition that can contain a bioactive factor, where the soluble soft tissue protein composition is made by a method that can include the steps of methods of making a soluble soft tissue protein composition that can include the steps of harvesting soft tissue from a donor to obtain harvested soft tissue, where the soft tissue contains soft tissue cells; heating the harvested soft tissue to at least 20° C.; and lysing the soft tissue cells to obtain a soft tissue cell lysate to yield the soluble soft tissue protein composition. The subject in need thereof can have soft tissue damage. The subject in need thereof can be in need of a soft tissue graft. The subject in need thereof can be in need of a soft tissue augmentation.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
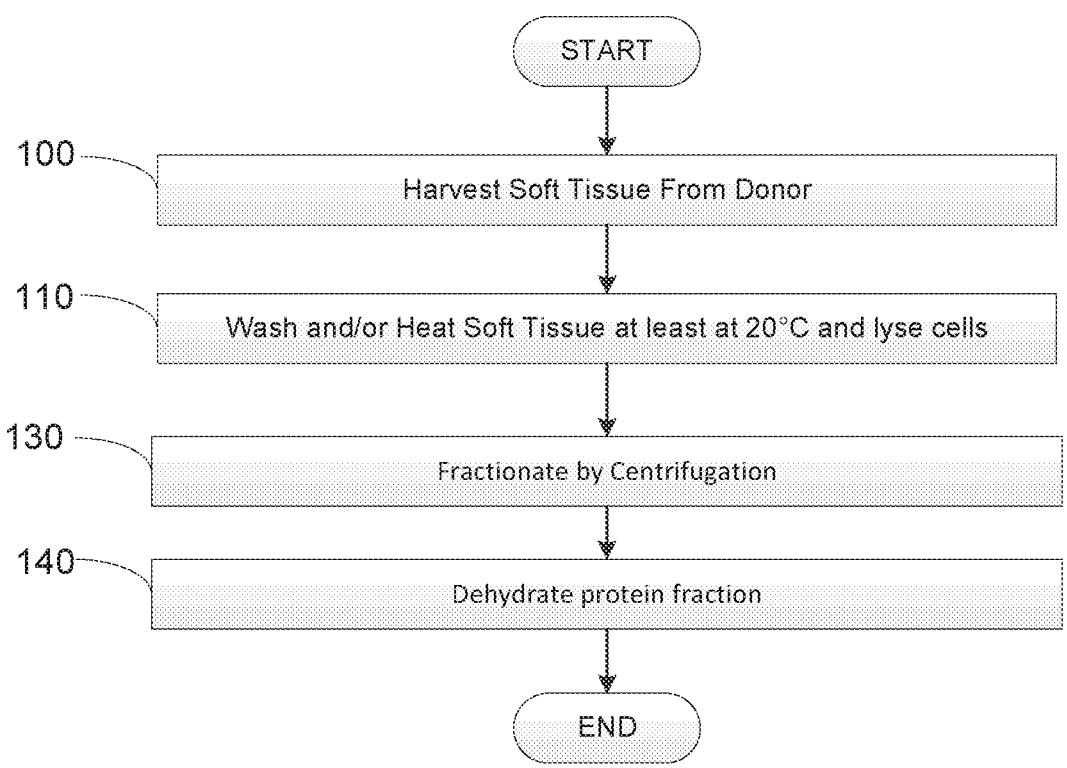
FIG. 1 is a flow diagram showing one embodiment of a method to produce soluble soft tissue protein compositions.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

As used herein, "about," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

As used herein, "effective amount" is an amount sufficient to effect beneficial or desired results. An effective amount can be administered in one or more administrations, applications, or dosages.

As used herein, "therapeutic" refers to treating or curing a disease or condition.

As used herein, "adipocyte" refers to a cell type also known as a lipocyte or fat cell. Adipocytes are the cells that primarily compose adipose tissue, specialized in storing energy as fat.

As used herein, "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

As used herein, "preventative" refers to hindering or stopping a disease or condition before it occurs or while the disease or condition is still in the sub-clinical phase.

As used herein, "concentrated" used in reference to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "isolated" means separated from constituents, cellular and otherwise, with which the polynucleotide, peptide, polypeptide, protein, antibody, or fragments thereof, are normally associated in nature. A non-naturally occurring polynucleotide, peptide, polypeptide, protein, antibody, or fragments thereof, does not require "isolation" to distinguish it from its naturally occurring counterpart.

As used herein, "diluted" used in reference to an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "biocompatible" or "biocompatibility" refers to the ability of a material to be used by a patient without eliciting an adverse or otherwise inappropriate host response in the patient to the material or a derivative thereof, such as a metabolite, as compared to the host response in a normal or control patient.

As used herein, "cell," "cell line," and "cell culture" include progeny. It is also understood that all progeny may not be precisely identical in DNA content, due to deliberate or inadvertent mutations. Variant progeny that have the same function or biological property, as screened for in the originally transformed cell, are included.

As used herein, "specific binding" refers to binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

As used herein, "control" is an alternative subject or sample used in an experiment for comparison purposes and included to minimize or distinguish the effect of variables other than an independent variable.

As used herein, "positive control" refers to a "control" that is designed to produce the desired result, provided that all reagents are functioning properly and that the experiment is properly conducted.

As used herein, "negative control" refers to a "control" that is designed to produce no effect or result, provided that all reagents are functioning properly and that the experiment is properly conducted. Other terms that are interchangeable with "negative control" include "sham," "placebo," and "mock."

As used herein, "culturing" refers to maintaining cells under conditions in which they can proliferate and avoid senescence as a group of cells. "Culturing" can also include conditions in which the cells also or alternatively differentiate.

As used herein, "synergistic effect," "synergism," or "synergy" refers to an effect arising between two or more molecules, compounds, substances, factors, or compositions that is greater than or different from the sum of their individual effects.

As used herein, "additive effect" refers to an effect arising between two or more molecules, compounds, substances, factors, or compositions that is equal to or the same as the sum of their individual effects.

As used herein, "autologous" refers to being derived from the same subject that is the recipient.

As used herein, "allograft" refers to a graft that is derived from one member of a species and grafted in a genetically dissimilar member of the same species.

As used herein "xenograft" or "xenogeneic" refers to a substance or graft that is derived from one member of a species and grafted or used in a member of a different species.

As used herein, "autograft" refers to a graft that is derived from a subject and grafted into the same subject from which the graft was derived.

As used herein, "allogeneic" refers to involving, derived from, or being individuals of the same species that are sufficiently genetically different so as to interact with one another antigenically.

As used herein, "syngeneic" refers to subjects or donors that are genetically similar enough so as to be immunologically compatible to allow for transplantation, grafting, or implantation.

As used herein, "implant" or "graft," as used interchangeably herein, refers to cells, tissues, or other compounds, including metals and plastics, that are inserted into the body of a subject.

As used herein, "filler" refers to a substance used to fill a cavity or depression. The filler can fill the depression such that it is level with the surrounding area or that the cavity is filled, such that the depth of the depression or volume of the cavity is decreased, or such that the area that was the depression is now raised relative to the areas immediately surrounding the depression.

As use herein, "immunogenic" or "immunogenicity" refers to the ability of a substance, compound, molecule, and the like (referred to as an "antigen") to provoke an immune response in a subject.

As used herein, "exogenous" refers to a compound, substance, or molecule coming from outside a subject or donor, including their cells and tissues.

As used herein, "endogenous" refers to a compound, substance, or molecule originating from within a subject or donor, including their cells or tissues.

As used herein, "bioactive" refers to the ability or characteristic of a material, compound, molecule, or other particle that interacts with or causes an effect on any cell, tissue and/or other biological pathway in a subject.

As used herein, "bioactive factor" refers to a compound, molecule, or other particle that interacts with or causes an effect on any cell, tissue, and/or other biological pathway in a subject.

As used herein, "physiological solution" refers to a solution that is about isotonic with tissue fluids, blood, or cells.

As used herein, "donor" refers to a subject from which cells or tissues are derived.

As used herein, "extra cellular matrix" refers to the non-cellular component surrounding cells that provides support functions to the cell including structural, biochemical, and biophysical support, including but not limited to, providing nutrients, scaffolding for structural support, and sending or responding to biological cues for cellular processes such as growth, differentiation, and homeostasis.

As used herein, "complete extracellular matrix" refers to extracellular matrix that has all components (proteins, peptides, proteoglycans, and the like) present and may or may not include other cells that are embedded in the extra cellular matrix.

As used herein, "decellularized extracellular matrix" refers to complete extracellular matrix that has been processed to remove any cells embedded within the extracellular matrix.

As used herein, "extracellular matrix component" refers to a particular component. By way of a non-limiting example, an extracellular matrix comportment can be a specific class of comments (e.g. proteoglycans) or individual component (e.g. collagen I) that is separated or isolated from the other extracellular components. These components can be made synthetically.

As used herein "hydrogel" refers to a network of hydrophilic polymer chains that are dispersed in water. "Hydrogel" also includes a network of hydrophilic polymer chains dispersed in water that are found as a colloidal gel.

As used herein "self-assembling peptides" refer to peptides which undergo spontaneous assembly into ordered nanostructures. "Self-assembling peptides" include di-peptides, lego peptides, surfactant peptides, molecular paint or carpet peptides, and cyclic peptides.

DISCUSSION

Soft tissue grafting and implants play a role in cosmetic, reconstructive, and dental procedures. Many compositions and materials have been developed for use in soft tissue grafting and implants. Such materials include, but are not limited to, autograft, allograft, and synthetic bone graft materials. While these materials have enjoyed a certain amount of clinical success, donor morbidity when using autograft materials, adverse recipient immune response when using allograft materials, and adverse effects (e.g. scarring or other undesirable results) when using synthetic materials.

With the aforementioned shortcomings in mind, described herein are soluble soft-tissue protein compositions. The soluble soft-tissue protein compositions provided herein can, in some embodiments, overcome one or more of the shortcomings of existing soluble soft-tissue protein compositions. Also provided herein are methods of making the soluble soft tissue protein compositions. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Methods of Making the Soluble Soft Tissue Protein Compositions

Described herein are methods for producing compositions containing non-recombinant (NR) soluble soft tissue proteins and/or other bioactive factor(s). The methods described herein can also result in a composition containing a dehydrated NR soluble soft tissue protein(s) and/or other bioactive factor(s). In some embodiments, the dehydrated NR soluble soft tissue protein(s) and/or other bioactive factor(s) can bind to a scaffold upon reconstitution, such as when the dehydrated soluble soft tissue protein composition comes in contact with a bodily fluid. The soluble soft tissue protein compositions prepared by the methods described herein can have a greater amount and/or concentration of soft tissue protein(s) and/or additional bioactive factor(s), and/or less immunogenicity than other osteoinductive/osteostimulatory compositions, implants, or devices incorporating complete soft tissue and/or other complete bodily fluids or tissues. The soluble soft tissue protein compositions can contain bioactive proteins.

Attention is first directed to FIG. 1, which shows an embodiment of a method of producing a soluble protein composition from soft tissue. The method can begin by harvesting soft tissue from a donor 100. The donor can be a cadaver or a living subject. The donor can be a cadaver or can be a living subject. The soft tissue can be autologous, allogeneic or xenogenic. The soft tissue can be harvested in any way generally known in the art. After the soft tissue has been harvested, the soft tissue can be washed 110 in a solution. The wash solution may contain water, saline, antibiotic, antiseptic, antifungal, or crystalloid solution. In some embodiments, the wash solution is only water. Washing can take place at least at 20° C. In some embodiments, washing takes place at about 20° C. to about 37° C. In further embodiments, washing takes place at about 20° C. to about 40° C. Heating the soft tissue during washing facilitates the separation adipocytes from other types of soft tissue cells. The washing/heating step can be performed under physical agitation in a shaker incubator. In some embodiments, shaking can be conducted at about 10-300 rpm for up to about 24 hours.

During washing/heating 110, the soft tissue derived cells can be lysed. In some embodiments, the soft tissue derived cells can be lysed using a lysing solution containing an acid. In some embodiments the lysing solution can be just water. In some embodiments, the washing solution and the lysing solution can be the same solution. The acid can be acetic acid, formic acid, trichloroacetic acid, hydrofluoric acid, hydrocyanic acid, hydrogen sulfide, or hydrochloric acid. In some embodiments, the lysis solution contains about 0.001 M to about 1 M acetic acid. In some embodiments the lysing solution that contains the soft tissue is mixed with preheated water. In some embodiments, the soft tissue can be lysed for about 60 minutes. In other embodiments, the soft tissue is incubated in the lysing solution with shaking. In other embodiments, the lysing conditions can include, but are not limited to, ultrasonic techniques, thermolysis (e.g. freeze/thaw cycling), microfluidic techniques, osmotic shock, electric shock, homogenization, French press, impingement, excessive shear (e.g. aggressive pipetting through a small aperture, centrifuging at excessive revolutions per minute resulting in high gravity forces), pressure, vacuum forces, milling or bead beating techniques that physically collide or grind cells to mechanically break cell membranes, pH shock, exposure to detergents, enzymes, viruses, solvents, surfactants, hemolysins, or combinations thereof.

After washing/lysing 110, the lysate can be optionally fractionated via centrifugation 130 to separate out particles present in the lysate based on their size and/or density. Such centrifugation techniques that can be employed include, but are not limited to, differential centrifugation, rate-zonal centrifugation, and isopycnic centrifugation. In embodiments where centrifugation is used to separate particles in the lysate based on density, a suitable density gradient medium can be used. Suitable density gradient mediums include, but are not limited to, sucrose, glycerol, sorbitol, Ficoll® medium, polysucrose, dextrans, CsCl, $Cs_2SO_4$, KBr, Diatrizoate, Nycodenz® medium, Histodenz™ medium, iodixanol, Histopaque® mediums, ACCUSPI® medium, and Percoll® medium. One of ordinary skill in the art will appreciate that the type of medium used is dependent on the type of particle(s) that is desired to be separated out. One or more rounds of centrifugation can be applied to the lysate to further separate out different particles in the lysate. In some embodiments, the desired fraction contains a bioactive factor, such as, but not limited to, a cytokine. In some embodiments, the lysate is centrifuge at about 100 to about 20000 rpm for about 1 to about 600 minutes. In some embodiments, the lysate is centrifuged at about 4000×g for about 10 minutes at about 4° C.

After optional fractionation 130, the desired fraction can be removed from the centrifuged lysate. In some embodiments, the desired fraction contains one or more bioactive factor, such as, but not limited to, a cytokine. The protein/bioactive factor containing fraction can then be dehydrated 140 using a suitable technique. Suitable dehydrating techniques include, but are not limited to, evaporation, vacuum drying, lyophilization, freeze drying, sublimation, and precipitation. The protein/bioactive factor containing fraction can be 0% to 100% dehydrated. After dehydration, the soluble soft tissue protein composition can contain an acid that can be diluted and/or reconstituted along with the proteins and other bioactive factors that can be present in the soluble soft tissue protein composition. In some embodiments, the protein/bioactive factor containing fraction is not dehydrated, but is kept in as a liquid and refrigerated or frozen. In some embodiments, the protein/bioactive factor containing fraction can be flash frozen in liquid nitrogen or slow frozen by placing at a temperature below 0° C., such as −10, −20, −50 or -80° C.

Figure 2:
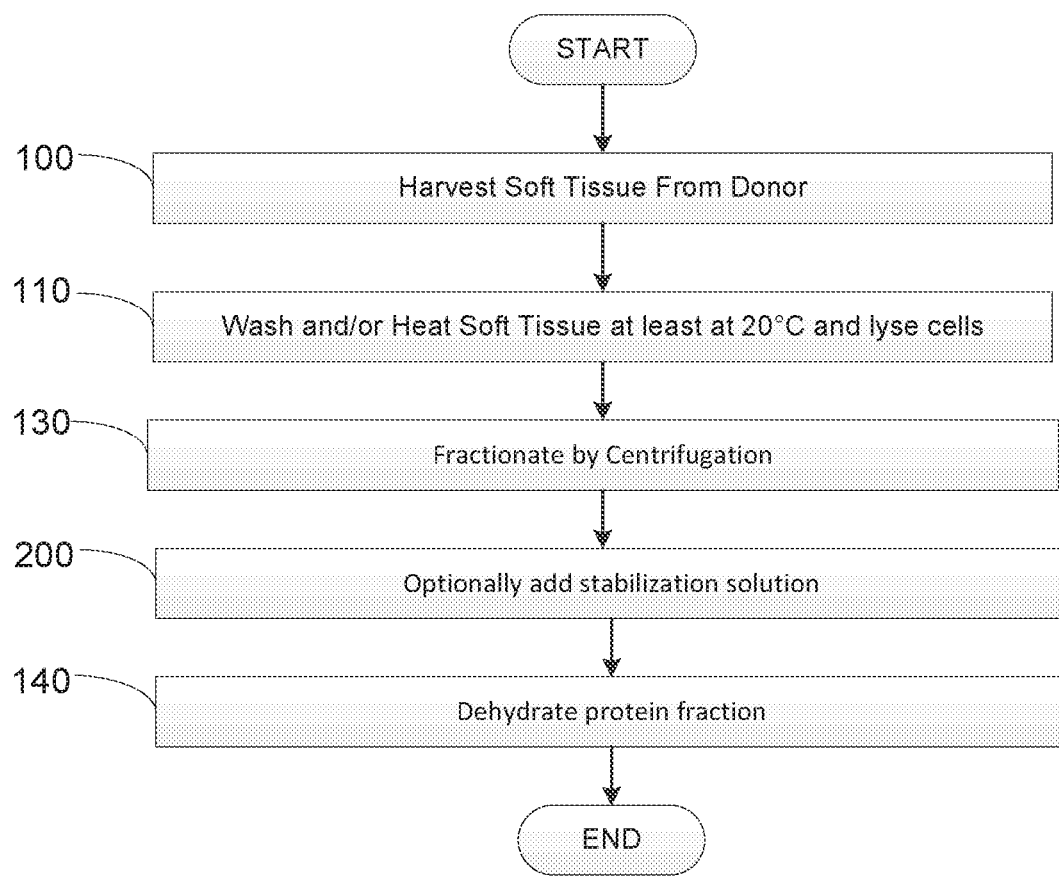
FIG. 2 is a flow diagram showing another embodiment of a method to produce soluble soft tissue protein compositions.

With the general process described, attention is directed to FIGS. 2-10, which demonstrate various embodiments of the general method of producing a soluble soft tissue derived soluble protein composition. Discussion begins with FIG. 2, which demonstrates embodiments of a method of generating a soluble soft tissue derived protein composition. As in FIG. 1, soft tissue can be harvested 100 and washed/heated 110 and soft tissue derived cells can be lysed. The desired components (e.g. bioactive factors) of the resulting lysate can be separated from the undesirable components using by fractionating using a suitable centrifugation technique 130. Once the desired fraction containing the proteins and/or bioactive factors of interest is obtained, the desired fraction can be dehydrated 140 using a suitable dehydration technique. As shown in FIG. 2, an optional suitable stabilization solution can be added 200 the dehydrated soft tissue derived soluble protein composition prior to dehydration 140. Suitable stabilization solutions can aid in maintaining protein integrity and activity. In some embodiments, the stabilizer can include sucrose, trehalose, glycine, L-glutamic acid, sodium chloride, polysorbate-80 and combinations thereof. The stabilization solution can contain preservatives, antibiotics, antivirals, antifungals, pH stabilizers, osmostablizers, anti-inflammants, anti-neoplastics, chemotherapeutics, immunomodulators, chemoattractants, growth factors, anticoagulants, or combinations thereof. In some embodiments, the stabilization solution per cc of final product can be about 1 mg Sucrose, 5 mg Glycine, 3.7 mg I-Glutamic Acid, 0.02 mg NaCl and 0.02 mg Polysorbate-80.

Figure 3:
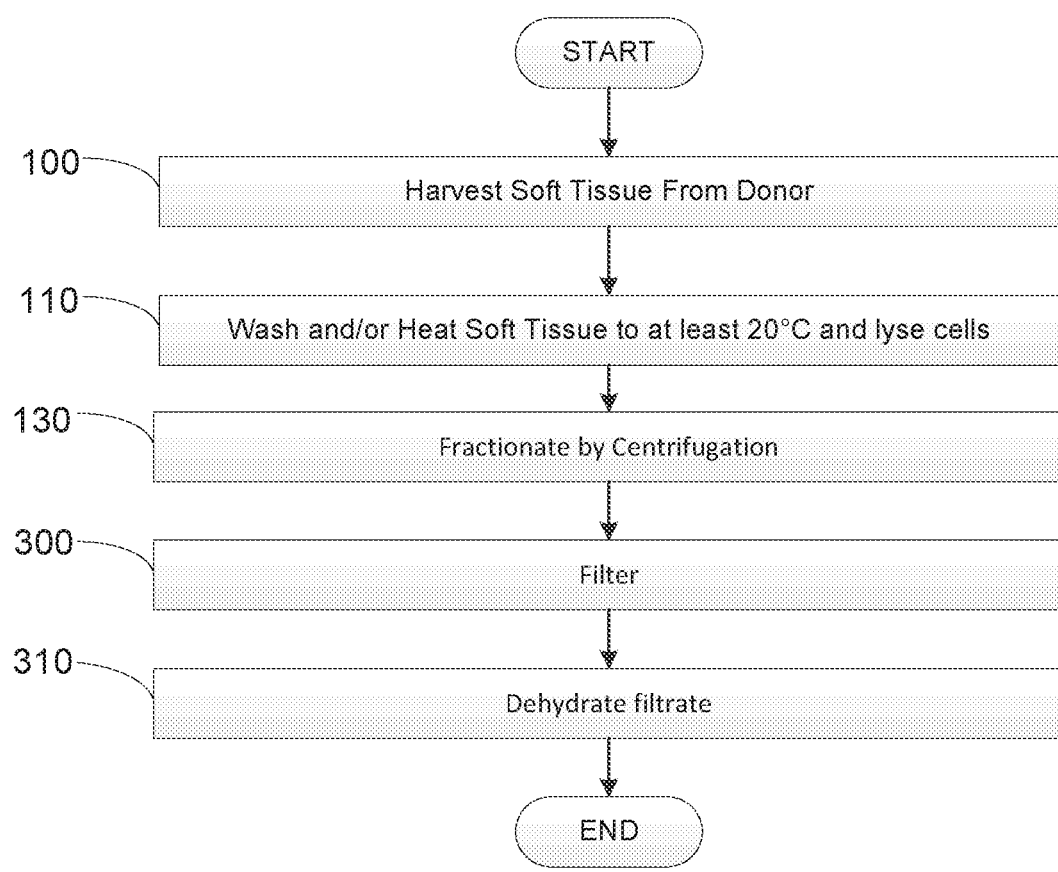
FIG. 3 is a flow diagram showing another embodiment of a method to produce soluble soft tissue protein compositions.

Discussion continues with FIG. 3, which shows another embodiment of a method of producing a soluble soft tissue derived soluble protein composition. As in FIG. 1, soft tissue can be harvested 100 and washed and heated and soft tissue cells can be lysed 110. The desired components (e.g. proteins and bioactive factors) of the resulting lysate can be separated from the undesirable components using by fractionating using a suitable centrifugation technique 130. As shown in FIG. 3, after fractionation by centrifugation 130 the fraction containing the desired components can be further filtered using a suitable filtration technique to remove additional undesired components that can remain in the fraction. Suitable filtration techniques can include, but are not limited to, size exclusion techniques and/or affinity purification techniques, immunoseparation techniques, and charged based separation techniques. In some embodiments, additional undesired components can include, but are not limited to, nucleic acids such as DNA and RNA, and other compounds such as hemoglobin, globin proteins, cell fragments, cell membrane molecules and other molecules that can stimulate an immune response in a subject. In some embodiments, the filter can be low protein binding. In some embodiments, the filter can be high DNA binding. In some embodiments, the filter can be high DNA binding.

Suitable materials for some filters used in the filtration step 300, include, but are not limited to, Teflon® membranes, nylon membranes, PVDF (polyvinylidene) membranes, polypropylene, cellulose acetate, PES (polyethersulfone), regenerated cellulose, glass fiber, and PTFE (polytetrafluorethylene. In some embodiments, the filter can have a size cutoff of about 0.1 to about 3.0 µM. In some embodiments multiple filters can be used, such as in a serial filtration system. In such a system, multiple types of filters can be used. The system can include at least two filters that differ in material and size cut offs. In some embodiments, polypropylene filters (e.g. size cut offs of 30 µm and 10 µm can be used), a glass fiber filter with a size cutoff of about 2.7 µm can be used, and/or a series of cellulose acetate filters (8 µm, 5 µm, 3 µm, 1.2 µm, 0.8 µm, 0.45 µm and final one of 0.2 µm) can be used to filter. The filters can be configured as syringe filters, disc filters, vacuum filter systems, bottle top vacuum filters, tube top vacuum filters, or centrifuge tube filters.

Figure 4:
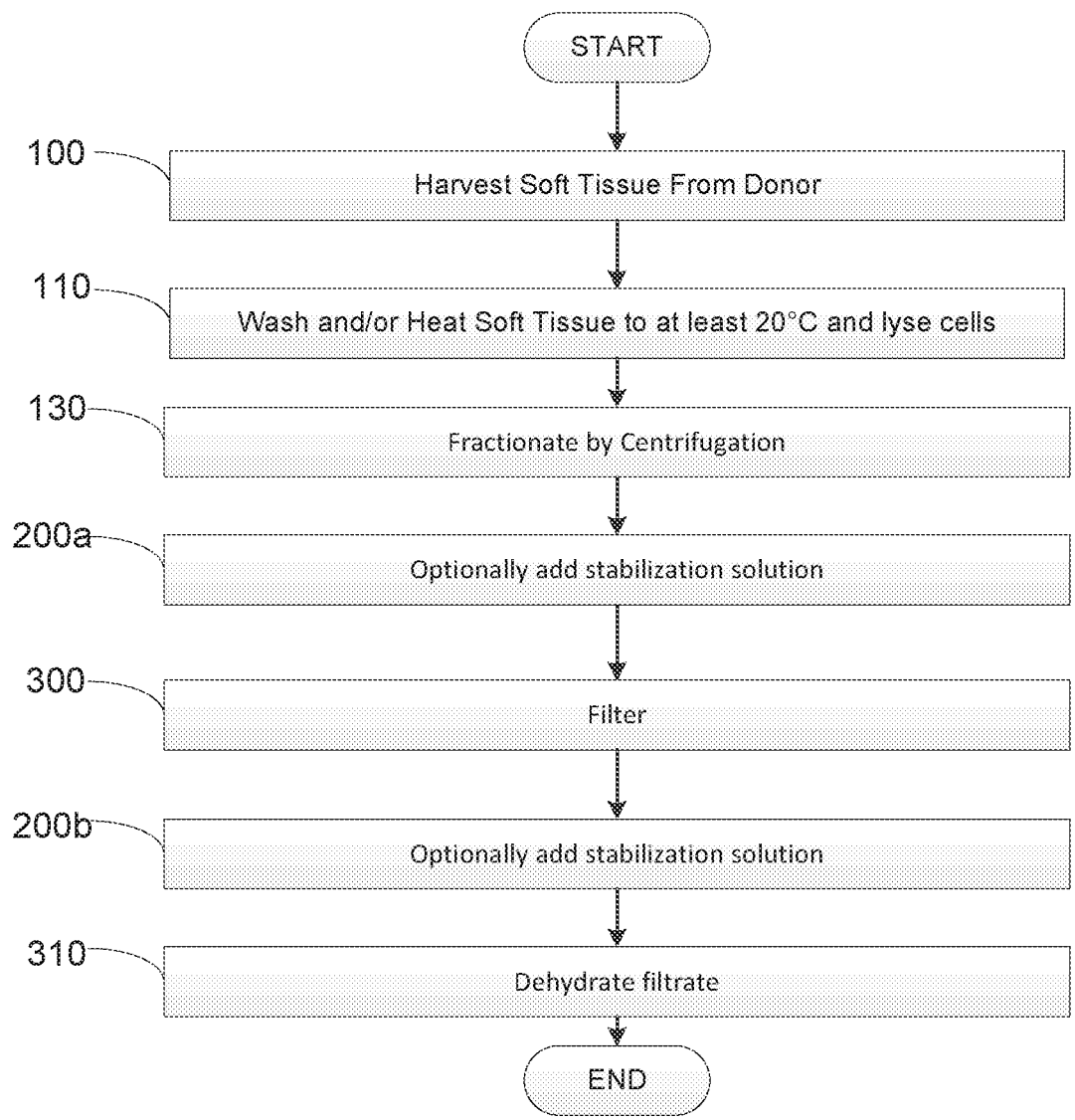
FIG. 4 is a flow diagram showing another embodiment of a method to produce soluble soft tissue protein compositions.

The filtrate obtained after filtering 300 can contain the desired soluble soft tissue proteins and/or other bioactive factors. The filtrate can also contain an acid. In some embodiments, the acid can be the acid that was used during the lysing step 110. The filtrate can be dehydrated 310 using any suitable dehydration techniques. Suitable dehydration techniques are described with respect to dehydrating the protein fraction 140 in FIG. 1. The filtrate can be 0% to 100% dehydrated during the dehydration step. As shown in FIG. 4, an optional suitable stabilization solution can be added 200a,b to the product prior to dehydration 310. The stabilization solution can be added after optional centrifugation 130 and/or after filtration 300. Suitable stabilization solutions are described elsewhere herein with respect to FIG. 2.

While the soft tissue can be heated 110 to facilitate better penetration of lysing solution and/or viscosity reduction and/or separation of adipocytes from other cells that can be present the soft tissue starting material, in some instances it can be desirable to filter the harvested soft tissue prior to lysing the soft tissue desired cells to further separate adipocytes or other cell types. In some embodiments the desired cell type can be adipocytes.

Figure 5:
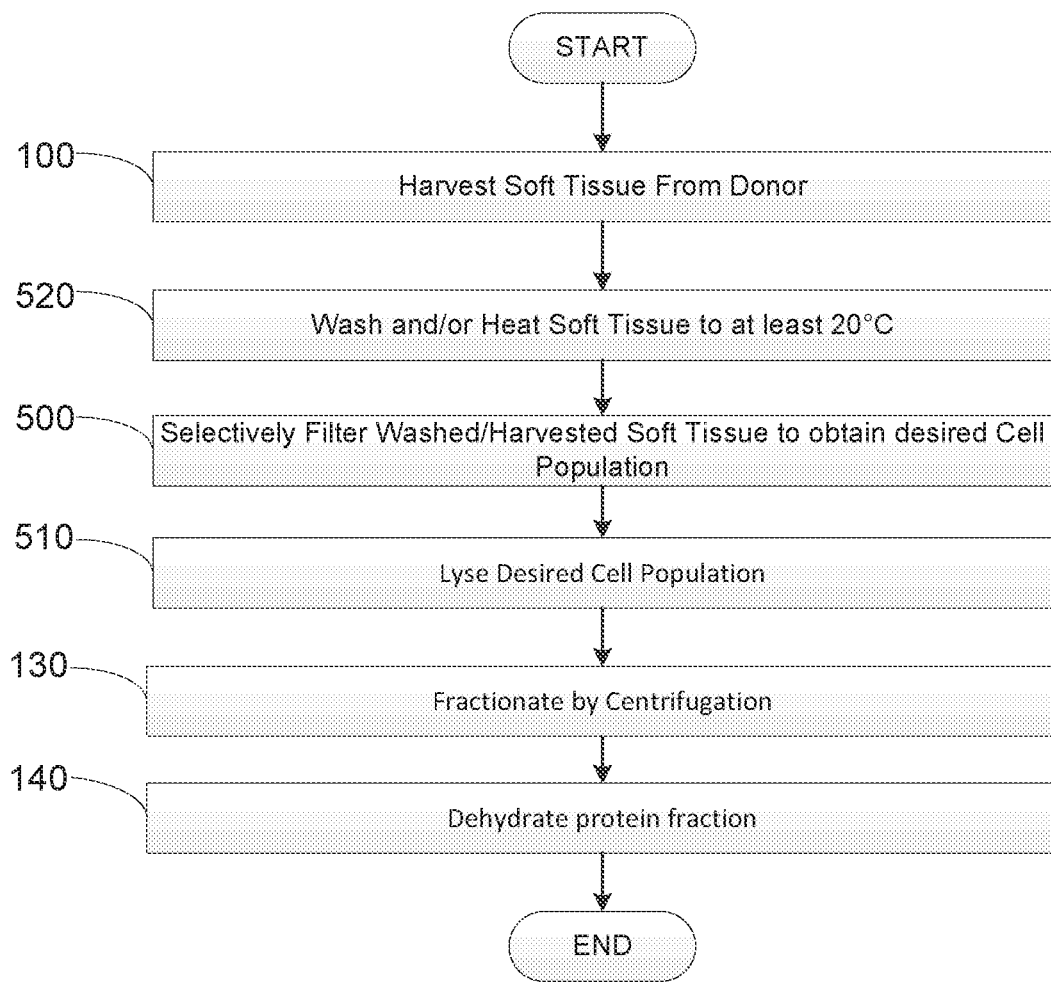
FIG. 5 is a flow diagram showing another embodiment of a method to produce soluble soft tissue protein compositions.

As shown in FIG. 5, soft tissue can be harvested 100 from a donor as previously described in reference to FIG. 1. The harvested soft tissue can then be washed/heated 520 as previously described with respect to FIG. 1. The washed/heated soft tissue can then be selectively filtered to obtain a desired cell population 500. The resulting desired cell population can be enriched for the desired cell type(s). In some embodiments, the resulting cell population is at least 50% to 100% of the desired cell type(s). Selective filtering can be completed by any suitable filtering techniques including, but not limited to, size exclusion separation techniques, affinity separation techniques, immunoseparation techniques, charge separation techniques, and chromatography techniques. For example, selective filtering can be achieved using osmotic lysis, cytolysis, centrifugation, size exclusion chromatography, ion exchange chromatography, expanded bed absorption chromatography, affinity chromatography (including but not limited to supercritical fluid chromatography), displacement chromatography, gas chromatography, liquid chromatography, column chromatography, planar chromatography (including, but not limited to paper chromatography, thin-layer chromatography), reverse-phase chromatography, simulated moving-bed chromatography, pyrolysis gas chromatography, fast protein liquid chromatography, high performance liquid chromatography, ultra-high performance liquid chromatography, countercurrent chromatography, chiral chromatography, and solid phase extraction. In some embodiments, where adipocytes are desired, the heating during the washing/heating step 520 is sufficient to be able to obtain an enriched population of adipocytes.

After selective filtering of the soft tissue derived cells 500, the remaining desired cell population is lysed 510. Suitable lysing techniques are described with respect to FIG. 1. After lysing, the desired cell population can be optionally fractionated 130 by centrifugation as previously described with respect to FIG. 1. Finally the obtained desired fraction containing the desired bone-marrow derived proteins and/or other bioactive factors can be dehydrated as previously described with respect to FIG. 1.

Figure 6:
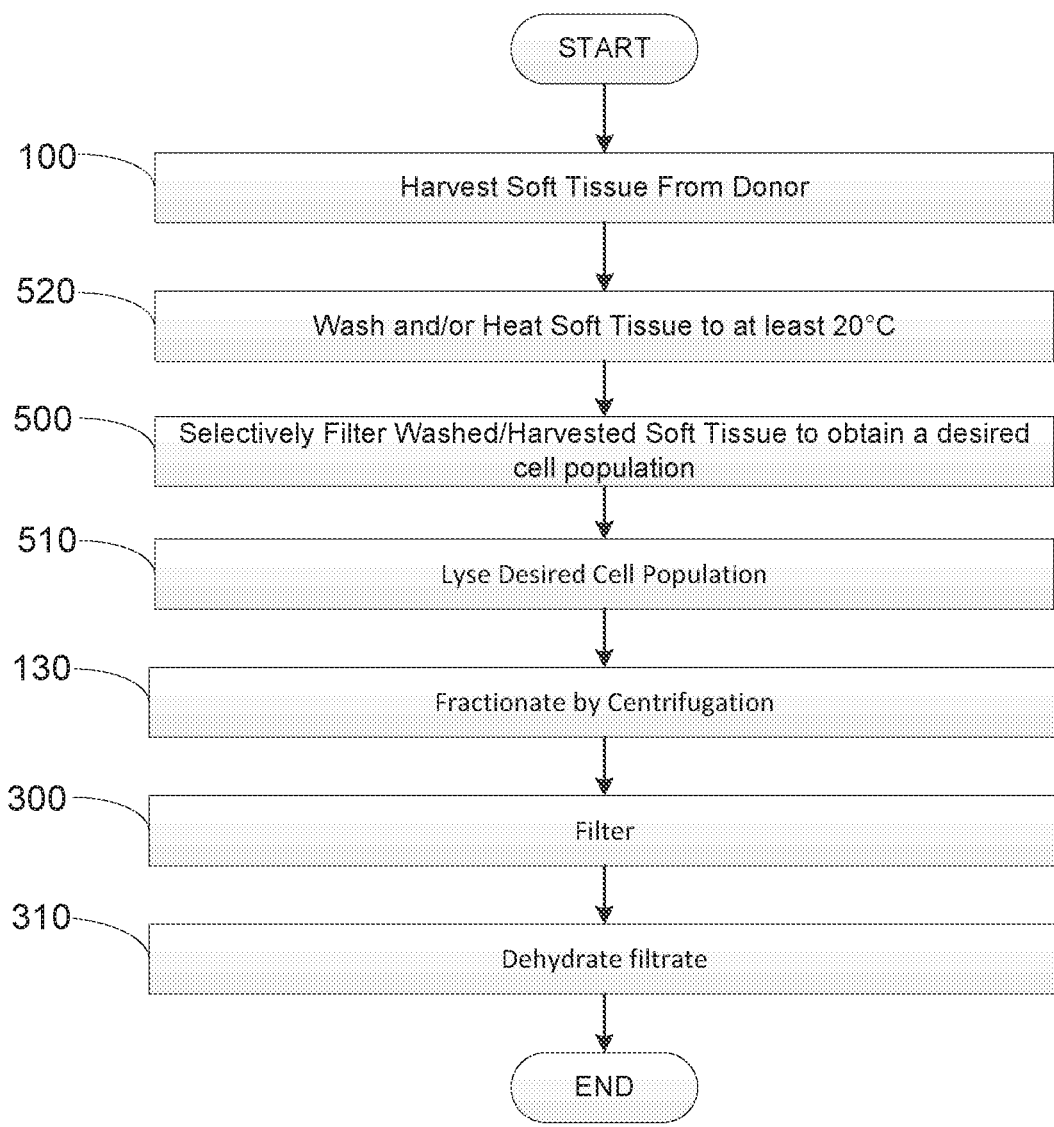
FIG. 6 is a flow diagram showing another embodiment of a method to produce soluble soft tissue protein compositions.
Figure 7:
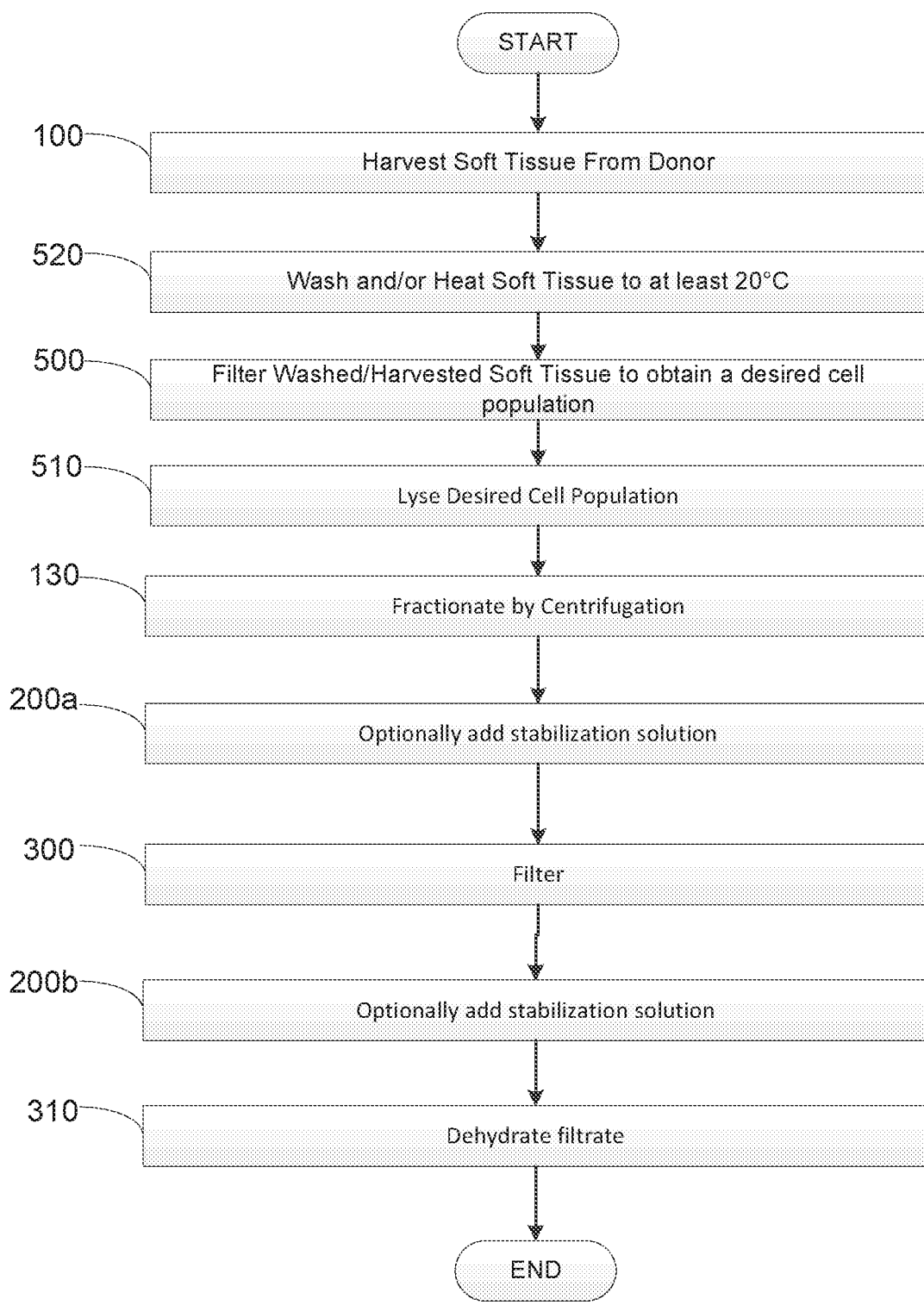
FIG. 7 is a flow diagram showing another embodiment of a method to produce soluble soft tissue protein compositions.

As shown in FIG. 6, the method where the harvested soft tissue can be selectively filtered 500 prior to lysing (FIG. 5) can optionally include the step of filtering 300 the obtained fraction after optional centrifugation 130. Filtering 300 can be performed as previously described with respect to FIG. 3. After filtering 300, the desired filtrate can be dehydrated 310 as previously described. As shown in FIG. 7, the methods (FIG. 5 and FIG. 6) where the harvested soft tissue can be selectively filtered 500 prior to or during lysing can also include the optional step of adding a stabilization solution 200 a,b after optional centrifugation 130 and/or filtration 300.

Figure 8:
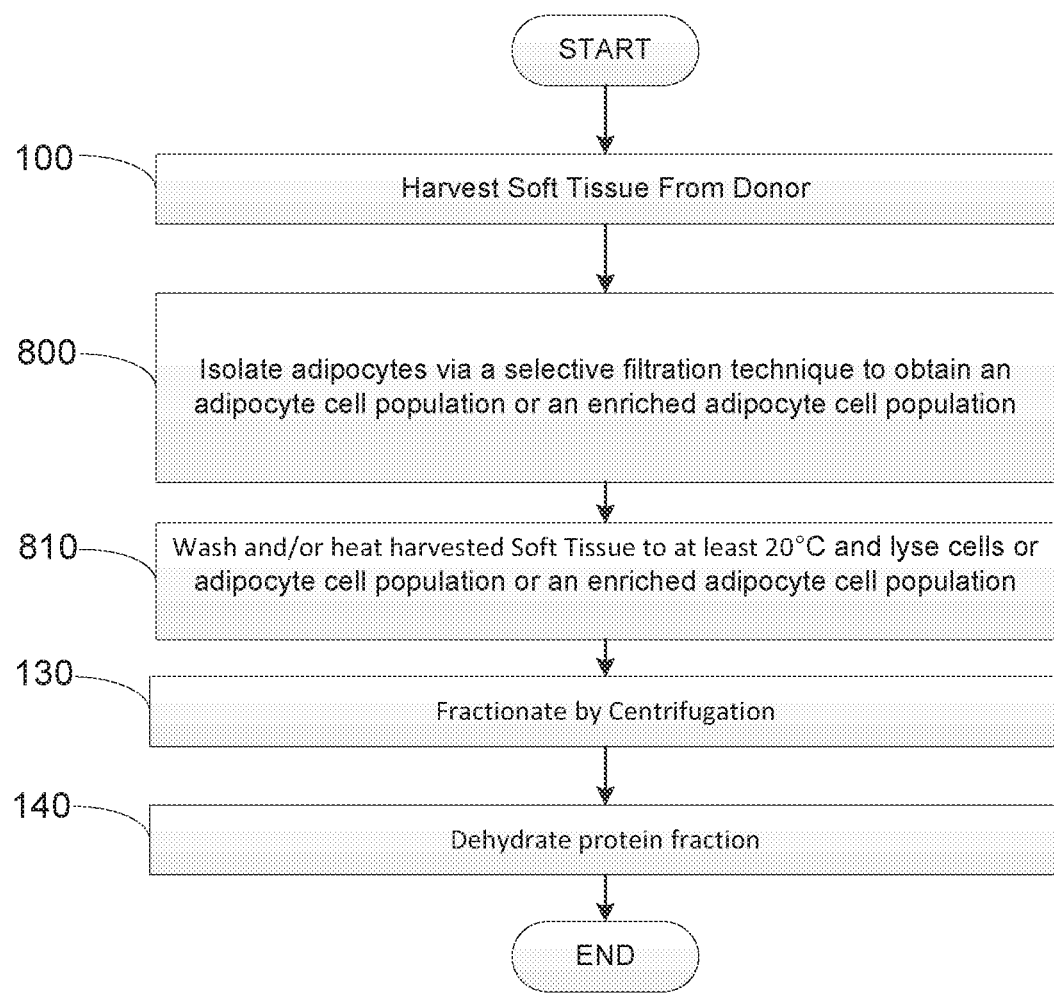
FIG. 8 is a flow diagram showing another embodiment of a method to produce soluble soft tissue protein compositions.

In some embodiments, it can be desirable to obtain proteins or bioactive factors specifically from adipocytes or other specific soft tissue cell type. As shown in FIG. 8, soft tissue can be harvested from a donor 100 as previously described in reference to harvesting soft tissue 100 in FIG. 1. Adipocytes or other soft tissue cell can be isolated via a selective filtration technique to generate an adipocyte (or other soft tissue cell) population or an enriched adipocyte (or other soft tissue cell) population 800. In some embodiments, the resulting adipocyte or other soft tissue cell population is about 50% to about 100% adipocytes or soft tissue cell. The harvested soft tissue or isolated soft tissue cells can be washed and lysed 810 as previously described in reference to FIG. 1, step 110. Suitable selective lysing techniques are described elsewhere herein, for example, in reference to FIG. 5. In some embodiments, heating is sufficient to separate adipocytes or other specific soft tissue cell from other undesired cells in the harvested soft tissue to obtain the desired adipocyte (or other soft tissue cell) cell population.

Figure 9:
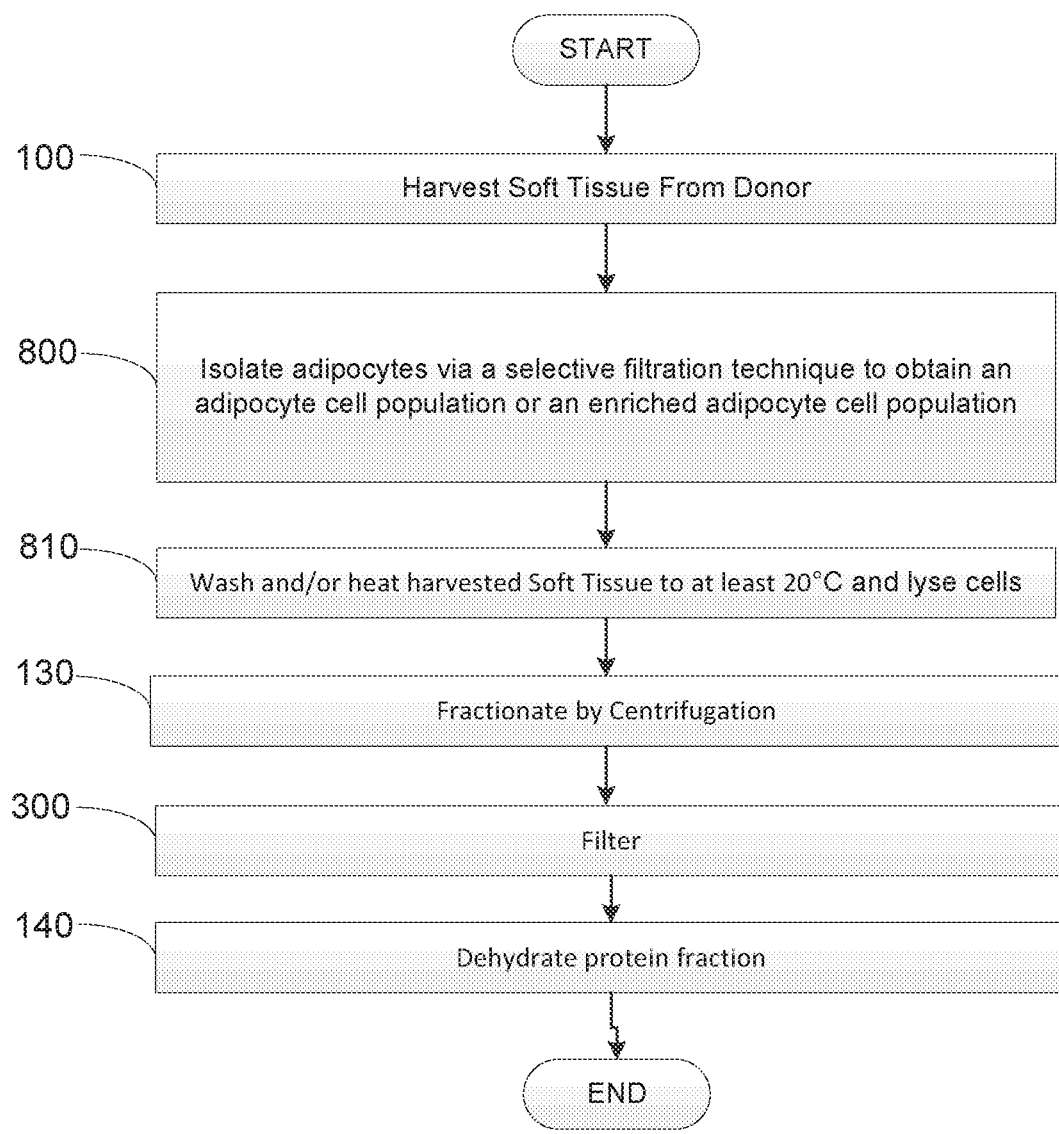
FIG. 9 is a flow diagram showing another embodiment of a method to produce soluble soft tissue protein compositions.
Figure 10:
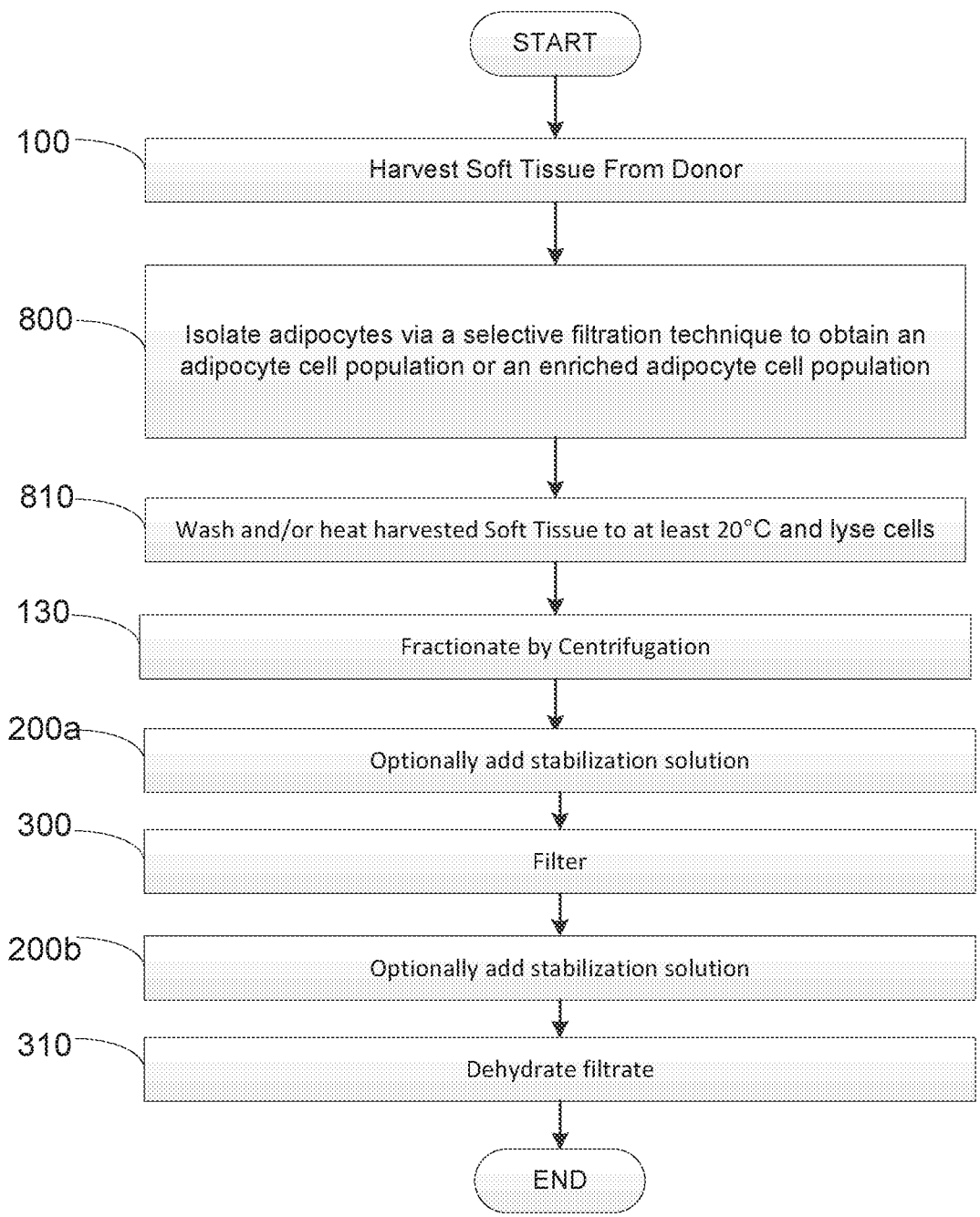
FIG. 10 is a flow diagram showing another embodiment of a method to produce soluble soft tissue protein compositions.

The adipocytes (or other soft tissue cell) or the cell population enriched for adipocytes (or other soft tissue cell) can be lysed 810 to obtain adipocyte or primarily adipocyte derived proteins and/or other bioactive factors. As previously described, the lysate can be fractionated by centrifugation 130 and the desired proteins and/or bioactive factor containing fraction can be dehydrated 140 as previously described. As shown in FIGS. 9 and 10, the method can include the optional steps of filtering 300 after optional centrifugation 130 and/or adding a stabilizer 200a,b after the step of optionally centrifuging 130 and/or filtering 300.

It will be appreciated that other steps can be included in any of the methods described herein. In some embodiments, the method can include a pH altering step where an acid, base and/or an acidic or basic solution can be added to product of any step in any method to result in a product that is acidic (pH less than 7), basic (pH greater than 7), or neutral (pH of 7). In some embodiments, after lysing, the lysate or product from any other subsequent step can be made more acidic, neutral, or basic as desired. In embodiments, the dehydrated product containing the soluble soft tissue derived proteins and/or bioactive factor(s) contains an acid that was introduced in the lysing step (e.g. 110, 510, or 810). In other embodiments, the stabilization solution can contain an acid or base that can result in an acidic, basic, or neutral solution. In some embodiments, the method can include a concentration step, where the product of any step in any embodiment of the method can be concentrated by a suitable concentration technique. Suitable concentration techniques include but are not limited to, dehydration techniques (described elsewhere herein) and centrifugation based techniques. Other concentration techniques will be appreciated by those of skill in the art.

Soluble Soft Tissue Protein Compositions

The soft tissue protein compositions can be harvested according to a method described herein from a suitable soft tissue. As used herein, "soft tissues" includes any tissue except for bone and bone marrow, and includes, but is not limited to, adipose tissue, muscle, cartilage, skin, tendons, ligaments, fascia, skin, fibrous tissue, synovial membranes, connective tissue, nerves, blood vessels, blood, lymph, and any organ.

The soluble bone soft tissue compositions can contain proteins and/or other non recombinant bioactive factors derived from cells present in the soft tissue, including but not limited to stem cells, adipocytes, myoblasts, myotubes, myocytes, chondroblasts, chondrocytes, fibroblasts, ganglion, nerve cells, glial cells (including macroglia and microglia), Schawann cells, astrocytes, oligodendrocytes, skin cells (e.g. keratinocytes, melanocytes, Merkel's cells, Langerhans' cells, stratum basale cells, prickle cells, and epithelial cells). The proteins can be intracellular proteins or membrane associated proteins. Such proteins include without limitation, bone morphogenetic proteins (BMPs) (e.g. BMP-1, BMP-2, BMP-3, BMP-4, BMP-5, BMP-6, BMP-7, BMP-8a, BMP-8b, BMP-10, and BMP-15), epidermal growth factor (EGF), insulin-like growth factors (IGFs) (e.g. IGF-1), fibroblast growth factors (FGFs) (e.g. aFGF (acidic fibroblast growth factor) and bFGF (basic fibroblast growth factor)), vascular endothelial growth factor (VEGF) osteoprotegerin (OPG), osteopontin (OPN), adipokines (e.g. resistin, adiponectin, leptin and apelin), fibrin, fibrinogen, other blood clotting factors (e.g. Factors), albumins, gloubulins, protein hormones, cytokines, chemokines, and nerve growth factorβ (NGFβ).

The soluble soft tissue protein composition can be 0% to 100% dehydrated. In some embodiments the soluble soft tissue protein composition can be about 100% dehydrated. The soluble soft tissue protein compositions do not inherently contain recombinant proteins. In some embodiments, the soluble bone soft tissue composition can be liquid or flowable solution. In some embodiments, the soluble soft tissue protein composition is frozen. The concentration of one or more of the bioactive factors in the soluble soft tissue protein compositions can be present in the composition at a concentration greater than or less than would be found in a cell within the body. The soluble soft tissue protein composition(s) as described herein can increase the efficiency of implant and/or graft integration and/or healing over that of the proteins if present in the context of complete soft tissue or other complete bodily fluid or tissue.

Additionally, the soluble soft tissue protein composition(s) described herein can lack the immunogenic proteins and other components that are present in complete soft tissue and/or other complete bodily fluid or tissue. The soluble soft tissue protein compositions provided herein, in some embodiments, do not include a recombinant or synthetic protein or other bioactive factor. In other words, in some embodiments the soluble soft tissue protein composition can be a non-recombinant soluble soft tissue protein composition.

Any given soft tissue protein and/or other bioactive factor can be present in the soluble soft tissue protein composition at a concentration of 0 µg/g to about 100 mg/g of isolated protein in the final product, dehydrated or otherwise provided.

Additionally, the soluble soft tissue protein composition can also contain an amount of a suitable acid. In some embodiments, the acid is a residual or other amount of the acid that can be used to lyse the soft tissue cells. In some embodiments, the acid can be acetic acid. Other suitable acids are described elsewhere herein. The acid can facilitate and/or increase binding of the proteins in the soluble soft tissue protein composition to a scaffold or other bodily tissue when the proteins are diluted or rehydrated during use, which is described elsewhere herein.

In some embodiments, soluble soft tissue protein composition can include a stabilizer composition or stabilizer compounds. Suitable stabilization compounds can include, but are not limited to preservatives, antibiotics, antivirals, antifungals, pH stabilizers, osmostablizers, anti-inflammants, anti-neoplastics, chemotherapeutics, immunomodulators, chemoattractants, growth factors, anticoagulants, or combinations thereof. The stabilization solution can increase shelf life of the soft tissue soluble protein composition and/or reduce denaturation of proteins during dehydration, sterilization, and/or storage. In addition, other materials, such as nitrogen, can be used to help reduce free radical formation and denaturation during sterilization. In some embodiments, the stabilization solution per cc of final product can be about 1 mg Sucrose, about 5 mg Glycine, about 3.7 mg l-Glutamic Acid, about 0.02 mg NaCl, and about 0.02 mg Polysorbate-80.

In some embodiments, a dehydrated or liquid soluble soft tissue protein composition can be reconstituted. This can result in a dilution of the bioactive factors within the dehydrated soluble soft tissue composition. In some embodiments, dehydration of a liquid soluble soft tissue protein composition can be dehydrated, which can result in a concentration of the proteins in the composition. The soluble soft tissue protein composition can be diluted/concentrated from 0.1 to 100 fold, 0.1 to 50 fold, 0.1 to 20 fold, or 0.1 to 5 fold.

In some embodiments, the final volume of a reconstituted or a liquid soluble soft tissue protein composition can be at least 1cc, or 1 cc to about 100 cc, about 1 cc to about 50 cc, 1 cc to about 25 cc, about 1 cc to about 20 cc, about 1 cc to about 10 cc. The final soluble soft tissue protein product can be dehydrated or reconstituted to achieve a desired volume or particular protein concentration or composition.

Methods of Using the Soluble Soft Tissue Protein Compositions

The soluble soft tissue protein compositions (dehydrated or otherwise formulated as described herein) can contain an acid or be at an acidic pH. The soluble soft tissue protein compositions can be implanted into or otherwise administered to a subject in need thereof. In some embodiments, an effective amount of the soluble soft tissue protein composition (dehydrated or otherwise formulated) can be implanted or otherwise administered to a subject in need thereof. When implanted or administered, the soft tissue proteins and/or other bioactive factors and the acid can be diluted and/or reconstituted by the bodily fluids of the subject. When this occurs, an acid microenvironment surrounding the proteins and/or other bioactive factors can be created. The acidic microenvironment surrounding the soluble soft tissue protein composition can facilitate solubilization of the soft tissue derived proteins and/or other bioactive factors in the composition and can also facilitate the binding of the soft tissue proteins and/or other bioactive factors a scaffold (natural or synthetic), bone, cartilage, or other tissue of the subject at the site where the soluble soft tissue protein composition is deposited within the subject.

The soluble soft tissue protein compositions (dehydrated or otherwise formulated as described herein) can be added to a suitable scaffold or device. Suitable scaffolds include, but are not limited to, allogeneic, autologous, syngeneic, or xenogeneic complete extracellular matrix, decellularized or acellular extracellular matrix, or extracellular matrix components, hydrogels, synthetic or natural polymer solids and semi-solids, carbohydrates, self-assembling peptides, carbon nanotubes, chitosan, alginate, hyaluronic acid, bone powder, cartilage powder, proteins, sugars, plastics, metals, or combinations thereof. In some embodiments, the scaffold can be biocompatible. In other embodiments, the scaffold can be allogeneic, xenogenic, or autologous bone or demineralized bone. The scaffold can be flowable or non-flowable.

Figure 11:
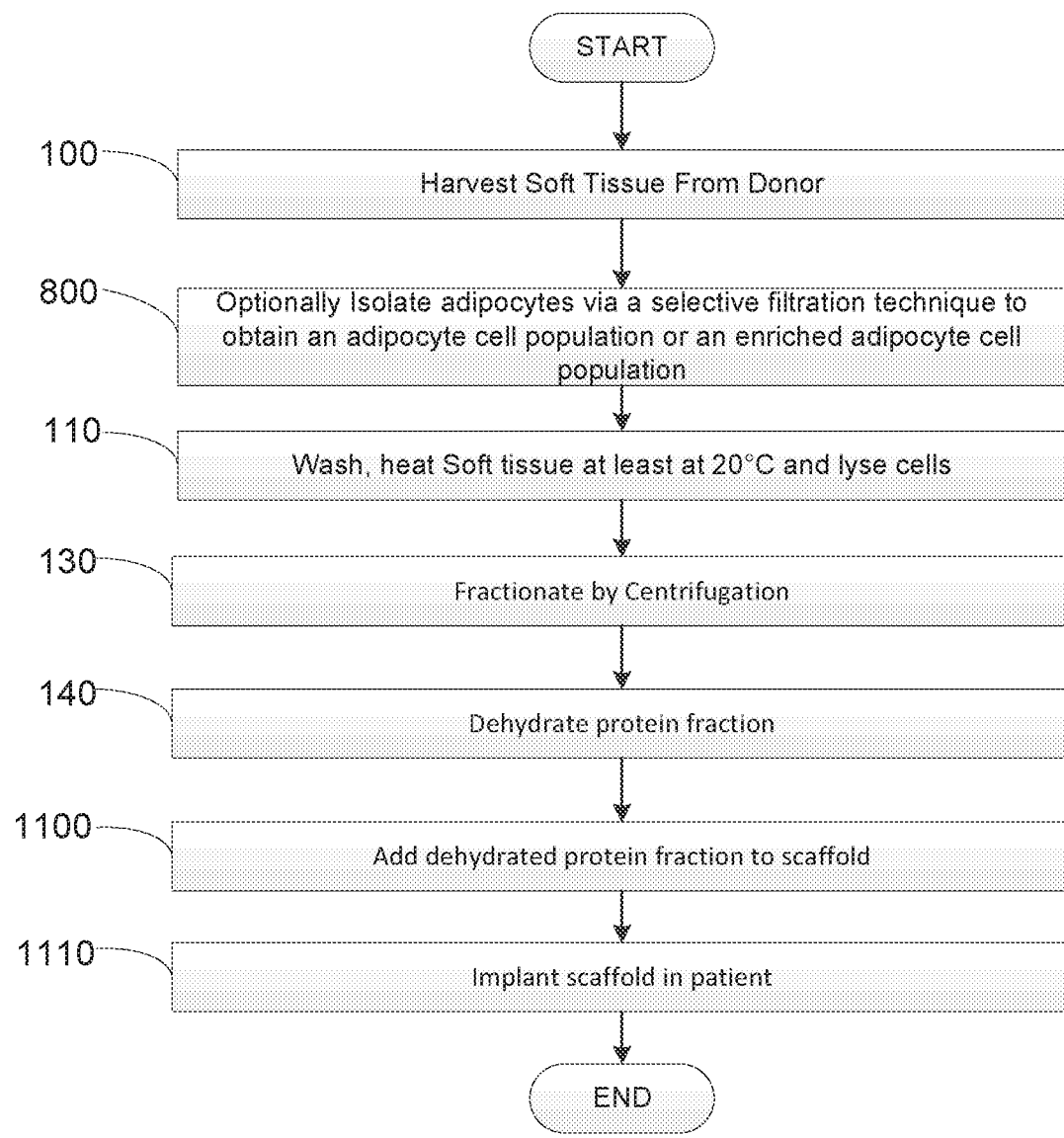
FIG. 11 is a flow diagram showing another embodiment of a method to produce soluble soft tissue protein compositions.

In some embodiments, the soluble soft tissue protein composition can be implanted or otherwise administered to a subject in need thereof without a scaffold material. In other embodiments, as shown in FIG. 11, the soluble soft tissue protein composition can be applied to a scaffold (implant) 1100, which is already present in a subject or can be implanted into a subject in need thereof 1110. When implanted 1110, the proteins in the dehydrated (or otherwise formulated) soluble soft tissue derived protein composition can solubilize and/or bind the scaffold when they come in contact a bodily fluid present in the subject. The acid present in the dehydrated (or otherwise formulated) soluble soft tissue derived protein composition can create an acidic microenvironment where the scaffold and/or soluble soft tissue protein composition is present. The acidic microenvironment can facilitate solubilization of the soft tissue derived proteins and/or binding of the proteins and/or other bioactive factors to the scaffold (synthetic or natural) and/or other bone or tissue of the subject that are at the site of implantation. In some embodiments, the soluble soft tissue protein composition can be added in a dehydrated state to an implant material to encapsulate the proteins such as a putty, gel, or suspension.

In other embodiments, the soluble soft tissue derived protein composition can be applied directly into a scaffold already present in the subject in need thereof. As previously described, the proteins and/or other bioactive factors can be diluted or reconstituted when contacted with a bodily fluid present within the subject. As also described above, the acid that can be present in the soft tissue protein compositions described herein can create an acidic microenvironment that can facilitate solubilization and/or binding of the soft tissue proteins and/or bioactive factors to a scaffold present in the subject.

In some embodiments, the method can include the step of implanting or otherwise administering a soluble soft tissue protein composition or scaffold incorporating a soluble soft tissue protein composition as described herein to a subject in need thereof. In some embodiments, a method of treating a subject in need thereof can include the step of implanting or otherwise administering a soluble soft tissue protein composition or scaffold incorporating a soluble soft tissue protein composition as described herein to the subject in need thereof. In some embodiments, the subject in need thereof needs a soft tissue graft or soft tissue augmentation.

What is claimed is:

1. A dehydrated soluble soft tissue protein composition comprising a bioactive factor, where the dehydrated soluble soft tissue protein composition is made by a method comprising:

harvesting soft tissue from a donor to obtain harvested soft tissue, where the soft tissue contains soft tissue cells;

heating the harvested soft tissue to at least 20° C.;

lysing the soft tissue cells by osmotic shock without a detergent to obtain a soft tissue cell lysate;

isolating the soft tissue lysate from the soft tissue to yield the soluble soft tissue protein composition; and dehydrating the soluble soft tissue lysate to obtain a dehydrated soluble soft tissue protein composition.

2. The soluble soft tissue protein composition of claim 1, further comprising the step of fractionating the soft tissue cell lysate via centrifugation to obtain a soluble soft tissue protein fraction after lysing the soft tissue cells.

3. The soluble soft tissue protein composition of claim 1, wherein heating the harvested soft tissue occurs at about 20° C. to about 40° C.

4. The soluble soft tissue protein composition of claim 1, further comprising the step of washing the harvested soft tissue.

5. The soluble soft tissue protein composition of claim 4, wherein the steps of washing the harvested soft tissue, heating the harvested soft tissue, and lysing soft tissue cells occur simultaneously.

6. The soluble soft tissue protein composition of claim 5, further comprising the step of applying an amount of the dehydrated soluble soft tissue protein composition in stabilization solution to a scaffold.

7. The soluble soft tissue protein composition of claim 1, further comprising the step of adding a stabilization solution prior to dehydrating.

8. The soluble soft tissue protein composition of claim 1, further comprising the step of filtering the soluble soft tissue protein fraction.

9. The soluble soft tissue protein composition of claim 1, further comprising the step of selectively filtering or isolating the soft tissue cells to obtain a desired cell population prior to lysing the soft tissue cells.

10. The soluble soft tissue protein composition of claim 9, wherein the step of lysing further comprises lysing the desired cell population.

11. The soluble soft tissue protein composition of claim 9, wherein the desired cell population is adipocytes.

12. The soluble soft tissue protein composition of claim 1, further comprising the step of applying an amount of the dehydrated soluble soft tissue protein composition to a scaffold.

13. A method of treating a subject in need thereof comprising implanting or administering a soluble soft tissue protein composition of claim 1.

14. The method of claim 13, wherein the subject in need thereof has soft tissue damage.

15. The method of claim 13, wherein the subject in need thereof is in need of a soft tissue graft.

16. The method of claim 13, wherein the subject in need thereof is in need of a soft tissue augmentation.

* * * * *